United States Patent [19]

Hill et al.

[11] 4,133,952

[45] Jan. 9, 1979

[54] PROCESS AND INTERMEDIATE FOR PREPARING AURANOFIN

[75] Inventors: David T. Hill, North Wales, Pa.; Ivan Lantos, Blackwood, N.J.; Blaine M. Sutton, Hatboro, Pa.

[73] Assignee: SmithKline Corporation, Philadelphia, Pa.

[21] Appl. No.: 805,496

[22] Filed: Jun. 10, 1977

[51] Int. Cl.$^2$ ............................................. C07H 23/00
[52] U.S. Cl. .................................... 536/121; 424/180; 536/4
[58] Field of Search .................................... 536/4, 121

[56] References Cited

U.S. PATENT DOCUMENTS

| 1,683,105 | 9/1928 | Schoeller et al. | 536/121 |
| 3,635,945 | 1/1972 | Nemeth et al. | 536/4 |

OTHER PUBLICATIONS

Sutton et al., "Jour. of Med. Chem.", vol. 15, No. 11, Nov. 1972, pp. 1095–1098.

*Primary Examiner*—Johnnie R. Brown
*Attorney, Agent, or Firm*—William H. Edgerton

[57] ABSTRACT

The S-gold salt of 2,3,4,6-tetra-O-acetyl-1-thio-$\beta$-D-glucopyranose reacts with triethylphosphine in an organic solvent to produce auranofin.

4 Claims, No Drawings

PROCESS AND INTERMEDIATE FOR PREPARING AURANOFIN

This invention comprises a new method for preparing the orally active gold containing antiarthritic agent, auranofin, which uses as starting material a new intermediate, S-gold-2,3,4,6-tetra-O-acetyl-1-thio-β-D-glucopyranose.

Auranofin has been demonstrated to be useful as an antiarthritic agent in man [J. Med. Chem. 15 1095 (1972); U.S. Pat. No. 3,635,945]. In these prior art references auranofin is prepared by reacting an alkali metal salt of a 1-thio-β-D-glucopyranose with a triethylphosphine gold halide. It also will be noted that the new intermediate S-gold salt used as starting material in this invention is the tetra acetyl derivative of the known gold compound aurothioglucose, see Merck Index 7th Ed. page 495. The invention claimed here is believed patentable over prior art known to the applicants.

The synthetic process here described may be illustrated by the following:

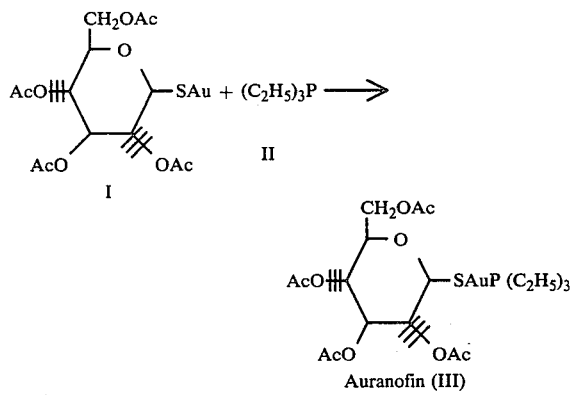

In this reaction, as is known to the art, Ac represents acetyl.

The method for preparing auranofin in the references referrred to above comprises reacting the potassium or sodium salt of 2,3,4,6-tetra-O-acetyl-1-thio-β-D-glucopyranose with triethylphospine gold (I) chloride in an aqueous alcohol solvent in the cold. The alkali metal salt starting material was generated from the 1-thiopseudourea derivative using sodium or potassium carbonate in water at below zero temperatures. We have now found that the gold salt of 2,3,4,6-tetra-O-acetyl-1-thio-β-D-glucopyranose can be prepared directly from its alkali metal salt by reaction with aurous chloride generated in situ from the reaction of gold acid chloride with thiodiglycol in the presence of an alkali metal base. This gold salt, never to our knowledge previously reported, reacts with tertiary phosphines readily under simple reaction conditions to give tertiary phosphine gold 2,3,4,6-tetra-O-acetyl-1-thio-β-D-glucopyranosides in excellent yield and purity.

The reaction of this invention is most conveniently carried out by reacting the new S-gold-2,3,4,6-tetra-O-acetyl-1-thio-β-D-glucopyranose with a stoichiometric amount of triethylphospine in an inert aprotic organic solvent in which the two reactants are soluble such as a common halogenated hydrocarbon solvent such as chloroform, carbon tetrachloride, ethylene tetrachloride or methylene chloride, a benzenoid solvent such as benzene, toluene or xylene, diethyl carbonate, dimethylformamide, dimethylacetamide, ethereal solvents such as diethyl ether or dioxane, ethylacetate, dimethyl sulfoxide, lower alkanols such as methanol, ethanol or isopropanol. Methylene chloride is a most convenient solvent.

The reaction most conveniently run and proceeds to completion at room temperature almost immediately. The desired auranofin is easily isolated and purified by methods known to the art.

The new gold salt (I) which is also part of this invention may also be prepared by other methods as will be apparent to those skilled in the art for example by O-acetylation of aurothioglucose (Solganol) but the methods detailed hereafter are simple and give excellent yields of pure product.

The reaction outlined above is generally applicable to the gold salts of any thio sugar especially their O-acylated or O-methylated derivatives as well as to any organic thiol which is capable of forming either a gold salt or a known alkali metal salt which can be converted into such a gold salt. Other thio sugars which may be substituted in equimolar quantities in the example are: hepta-O-acetylthiomaltose, thiofructose or thioglucofuranose.

The following example is to illustrate but not to limit this invention. Other modifications will be obvious to those skilled in the art. All temperatures are on the Centigrade scale.

EXAMPLE 1

Thiodiglycol 6.4 g (0.052 mole) in ethanol (20 ml) was added to 10 g (0.025 mole) of gold acid chloride trihydrate in water (50 ml) at 0°. To this was added, after filtering, a solution of 9.4 g (0.026 mole) of 2,3,4,6-tetra-O-acetyl-1-thio-β-D-glucopyranose and 6.6 g (0.048 mole) of potassium carbonate in 25 ml of ethanol and 60 ml of water. After stirring 1 hour at 0° (foaming) the precipitate was removed by filtration, washed with water and air-dried. Recrystallization from isopropanol-ether gave S-gold-2,3,4,6-tetra-O-acetyl-1-thio-β-D-glucopyranose as a light yellow solid, m.p. 146–148°; $[\alpha]_D^{25} = -56.9$ (1% methanol).

Triethylphosphine 0.2 g (1.7 mmole, 0.25 ml) was added to 1.0 g (1.7 mmole) of S-gold-2,3,4,6-tetra-O-acetyl-1-thio-β-D-glucopyranose in 6 ml of chloroform kept at room temperature. The solution immediately becomes colorless and after 15 minutes the solvent was removed at reduced pressure. Chromotagraphy (silica gel/ethyl acetate) gave 0.76 g of auranofin as a white solid which was recrystallized from methanol (3 ml) to give 0.55 g (45%) of product, m.p. 106°–108°; $[\alpha]_D^{25} = -56.1$ (1% methanol).

Equimolar quantities of the following tertiary phosphines may be substituted for triethylphosphine in this reaction such as butyldiethylphosphine, triallylphosphine, triisopropylphosphine, phenyldiethylphosphine, p-chlorophenyldiethylphosphine, p-methoxyphenyldiethylphosphine or diphenylethylphosphine.

What is claimed is:

1. The method of preparing auranofin comprising reacting S-gold-2,3,4,5-tetra-O-acetyl-1-thio-β-D-glucopyranose with a stoichiometric quantity of triethylphosphine in an inert aprotic organic solvent in which the two reactants are soluble.

2. The method of claim 1 in which the reaction is carried out at about room temperature in a halogenated hydrocarbon solvent.

3. The method of claim 2 in which the solvent is methylene chloride.

4. S-Gold-2,3,4,5-tetra-O-acetyl-1-thio-β-D-glucopyranose.

* * * * *